United States Patent [19]

Spohr

[11] Patent Number: 4,725,332

[45] Date of Patent: Feb. 16, 1988

[54] METHOD FOR MONITORING MICROHOLE GROWTH DURING PRODUCTION OF MICROHOLES HAVING A PREDETERMINED DIAMETER

[75] Inventor: Reimar Spohr, Darmstadt, Fed. Rep. of Germany

[73] Assignee: Gesellschaft für Schwerionenforschung mbH, Darmstadt, Fed. Rep. of Germany

[21] Appl. No.: 933,279

[22] Filed: Nov. 20, 1986

Related U.S. Application Data

[63] Continuation of Ser. No. 661,246, Oct. 15, 1984, abandoned.

[30] Foreign Application Priority Data

Oct. 13, 1984 [DE] Fed. Rep. of Germany ....... 3337227

[51] Int. Cl.⁴ .................. B44C 1/22; C03C 15/00; C03C 25/06; B29C 37/00
[52] U.S. Cl. ..................................... 156/626; 156/627; 156/628; 156/643; 156/644; 156/654; 156/668; 250/492.1
[58] Field of Search ............... 156/626, 627, 628, 643, 156/644, 654, 668; 252/79.1, 79.5; 378/160; 328/233; 250/472.1, 473.1, 492.1, 492.2, 492.3

[56] References Cited

U.S. PATENT DOCUMENTS

| 3,303,085 | 2/1967 | Price et al. ............. 156/657 X |
| 3,612,871 | 10/1971 | Crawford et al. ......... 156/643 X |
| 3,677,844 | 7/1972 | Fleischer et al. ......... 156/644 |
| 3,852,134 | 12/1974 | Bean ..................... 156/644 X |
| 4,369,370 | 1/1983 | Spohr .................... 378/160 |

FOREIGN PATENT DOCUMENTS 2717400 10/1978 Fed. Rep. of Germany ...... 156/628

Primary Examiner—William A. Powell
Attorney, Agent, or Firm—Spencer & Frank

[57] ABSTRACT

In a method for producing a substrate with microholes having a predetermined diameter, a test region on the substrate is irradiated with a significantly higher dosage of heavy ions than the rest of the substrate. During the development of the nuclear traces by etching, the surface of the substrate in the test region abruptly changes at a certain porosity. This macroscopically observable process is then utilized to interrupt the etching process after a precisely defined time, which is calibrated to provide microholes having a predetermined diameter on the remainder of the substrate.

7 Claims, 3 Drawing Figures

METHOD FOR MONITORING MICROHOLE GROWTH DURING PRODUCTION OF MICROHOLES HAVING A PREDETERMINED DIAMETER

This application is a continuation of application Ser. No. 661,246, filed Oct. 15, 1984, now abandoned.

BACKGROUND OF THE INVENTION

The present invention relates to a method for etching nuclear traces to obtain microholes having a predetermined diameter, with pluralities of nuclear traces and microholes, respectively, being produced simultaneously, for example, in a substrate such as a band-shaped foil or thin sheet.

Traditional machining techniques are incapable of producing very precise microholes, or extremely small apertures, in a substrate. Such microholes are useful, for example, in medicine, where a microhole about 5 microns in diameter can be used to determine the rigidity of individual red blood cells (diameter about 8 microns). Microholes can be produced in a substrate by irradiating the substrate with heavy ions from a particle accelerator to produce nuclear traces in the substrate, which is subsequently etched in order to develop microholes along the nuclear traces. For example, microholes can be produced in a polycarbonate foil 10 microns thick by irradiating the foil with $U^{238}$ ions having a specific energy of about 1 MeV/nucleon and thereafter exposing the foil to an etchant in the for of a normal NaOH solution with 10% ethanol at 40° C. The diameters of microholes depend upon a number of parameters, such as identity and thickness of the substrate, the etching time, etc.

U.S. Pat. No. 4,369,370 to Reimar Spohr, which is incorporated herein by reference, discloses a process for fabricating a single microhole produced from a nuclear trace by way of etching. However, during mass production of a band-shaped thin sheet having individualized holes with a diameter of less than a micron, it is rather time consuming to localize the individualized holes by way of a light or electron microscope so as to be able to monitor the diameter, during the etching process, and to terminate the process when the desired diameter has been reached.

SUMMARY OF THE INVENTION

It is the object of the present invention to provide a measuring procesw with which it is possible to shorten the microhole fabrication time and to simultaneously monitor a plurality of individual microholes with respect to their diameter during the etching process. It is then possible to terminate the etching process precisely at the desired diameter.

This is accomplished by the present invention by irradiating a band-shaped sheet or foil with a beam of heavy ions which is interrupted (that is, the beam is shutt off in order to terminate the irradiation at a predetermined dose value) to produce individual nuclear traces, using the beam to irradiate a separate test region on the sheet or foil at a higher dosage or density, jointly etching the individual nuclear traces and the bundle of traces in the test region under the same etching and developing conditions and terminating the etching process if there is a significant visual or electrical change in the test region, this change having previously been calibrated with respect to a predetermined microhole diameter. To interrupt the heavy ion beam an electrostatic, electromagnetic, or mechanical shutter may be used.

This method makes it possible in a simple manner to terminate the etching process precisely at the moment at which the microholes have reached the desired diameter, without having to check or monitor the individual holes.

DESCRIPTION OF THE PREFERRED EMBODIMENT

Figure 1:
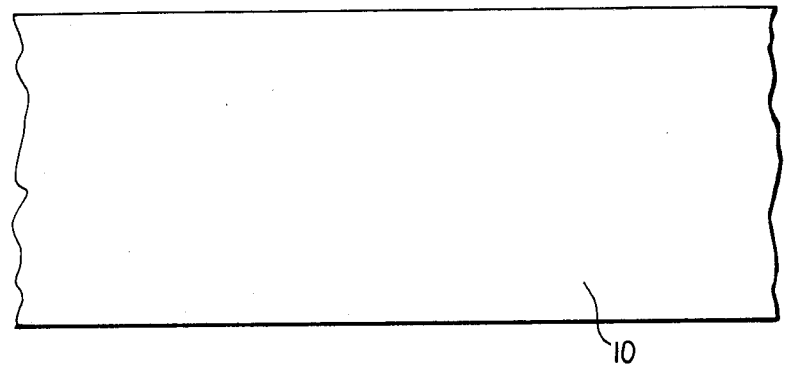
FIG. 1 illustrates a top plan view of a strip of film before irradiation thereof.

The method of the present invention, which is based on the statistical characteristics of etched nuclear traces, takes advantage of the discovery that samples which have been homogeneously irradiated with heavy ions, when subjected to a nuclear trace etching process, exhibit an abrupt change in optical characteristics which can be observed directly by visual means. Perforated samples can suddenly break through; that is, the nuclear traces are randomly distributed in the homogeneously irradiated region, some traces being clustered together and some being spaced further apart, so that as microholes develop around the traces during the etching process, some of the microholes will begin to overlap and the substrate will start to disintegrate. The optical transition occurs at a proximity of $P \lesssim 0.7$ (breakthrough at $P \gtrsim 1.0$ for throughgoing nuclear trace holes), with the porosity P being equal to the product of the number of holes and the surface area of the individual holes divided by the total area of the irradiated and lateretched:

$$P = \frac{\text{number of holes} \times \text{surface area of an individual hole}}{\text{total surface area of the irradiated and later etched material}}$$

For example, if the total surface area of the holes in one square unit of a substrate equals one-half unit square, so that the area of the remaining substrate between the holes also equals one-half unit square, the porosity would be 0.5. The surface area of an individual hole is the surface area of the hole produced after etching, or of the opening of a single etched channel in an otherwise intact region. In principle, the porosity P may be greater or smaller than 1.

The transition visually observed at a porosity of around 0.7 is based on the appearance of ring holes (that is, disintegrated regions forming closed paths around relatively intact regions) which, comparable to a phase transition, dissolve the continuity of the material interconnections. In thin samples, the occurrence of discrete islands of relatively intact material leads to a collapse of the mechanical characteristics on the irradiated surface and in thick samples to a great decrease in insulating characteristics or change in optical reflectivity. These transitions, which can be observed macroscopically or monitored by means of electrical measuring methods, are utilized to terminate the etching process at a precisely defined pore size of the etched nuclear traces.

For this purpose, the test region is placed onto the same thin sheet or web on which the individual holes are to be produced. Then the sheet portion on which the individual holes are to appear is irradiated simultaneously, with the irradiation of the test region. In this connection, as a practical matter, it is important to use the same foil, the same type of ions and the same energy for both irradiations (although in principle the types of ions and their energies may be different for the two irradiations). Only the dose, i.e. the particle density, should be significantly higher for the test region, e.g. $10^{11}$ ions per $cm^2$ for a full beam of argon or uranium ions or any other calibrated beam density value. Then both surfaces are etched under the same etching conditions until a significant change in optical or electrical characteristics of the above-described type occurs.

The irradiation of the test region and the region on which the individual holes are to appear, or calibrated region, may be simultaneous, or the irradiations may be at different times.

In the present invention, the system is calibrated before the production of microholes having a predetermined diameter begins. This calibration is accomplished by conducting trial runs under various conditions and measuring the individual microhole diameter when the macroscopic transition occurs. By selecting certain etching parameters and/or a certain radiation density, after the system is calibrated in this manner, one can produce individual microholes which have attained a predetermined diameter at the moment that the macroscopic observable transition in the test region occurs.

The macroscopic transition is utilized to terminate the process once the desired hole diameter has been reached. It is important in this process that the same etching and development conditions exist on the test region and on the normal surface provided with the individual holes, and that the test region is irradiated with a defined dosage.

Figure 2:
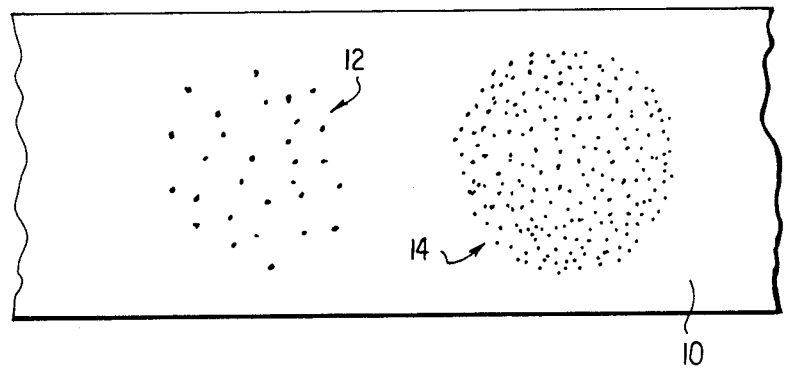
FIG. 2 schematically illustrates the film of FIG. 1 after it has been irradiated at a test region and at a calibrated region.
Figure 3:
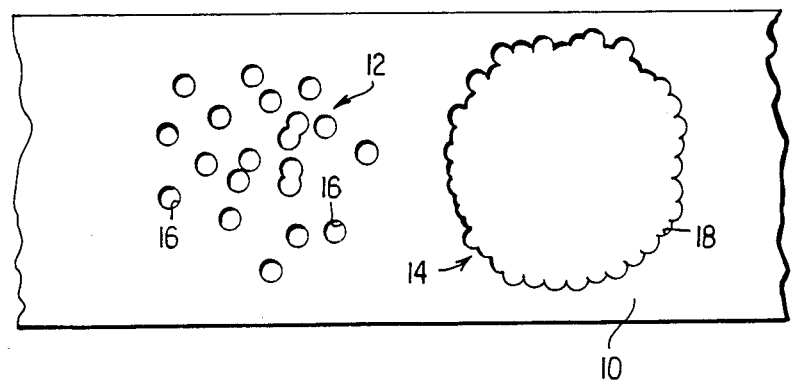
FIG. 3 schematically illustrates the irradiated film of FIG. 2 after it has been etched.

The principle of the invention is illustrated in the Figures. FIG. 1 represents a portion of a sheet of film 10 of nuclear track sensitive material before irradiation. FIG. 2 schematically illustrates sheet 10 after irradiation at calibrated region 12 and test region 14. In FIG. 2 the latent tracks are indicated as dots in regions 12 and 14, although the tracks are not visible to the naked eye. FIG. 3 illustrates film 10 after the etching process. The calibrated region 12 has obtained etched nuclear tracks 16 of calibrated diameters; tracks 16 are illustrated schematically as small circles although they are normally too small to be observed by the naked eye. Test region 14 contains more etched tracks. In FIG. 3 these etched tracks are overlapped and thus the material of film 10 has been removed from the test region 14, leaving a macroscopic hole 18 as a macroscopically observable property change. Examples of other macroscopically observable changes which might be used instead are mechanical strength, light transmission, electrical conductivity, etc.

It will be understood that the above description of the present invention is susceptible to various modifications, changes and adaptations, and the same are intended to be comprehended within the meaning and range of equivalents of the appended claims.

What I claim is:

1. A method for monitoring microhole growth while producing a substrate having microholes with a predetermined diameter, comprising:
    irradiating a first region on the substrate with an interrupted beam producing a given dosage of heavy ions of a given type and energy to produce individual nuclear traces in the first region;
    irradiating a separate second region on the substrate with a dosage of ions higher than the given dosage to produce a bundle of nuclear traces in the second region, the second region serving as a test region and being irradiated with ions of the same type and energy as the ions used to produce the individual nuclear traces in the first region so that the second region can subsequently be employed for monitoring;
    jointly etching the first and second regions under the same etching conditions for both;
    monitoring the progress of the etching in the first region by observing the second region to detect a macroscopic change visible to the naked eye in the second region, said macroscopic change having previously been calibrated so that microholes originating from the individual nuclear traces in the first region have attained the predetermined diameter when the macroscopic change in the second region occurs; and
    discontinuing the etching process when the macroscopic change in the second region occurs in order to obtain microholes having the predetermined diameter in the first region.

2. The method of claim 1, wherein the step of irradiating the first region and the step of irradiating a separate second region on the substrate are conducted by irradiating one of a band-shaped sheet and a foil.

3. The method of claim 1, wherein the step of monitoring the progress of the etching comprises at least one of visually observing the second region to observe a macroscopic optical change and electrically monitoring the second region to detect a macroscopic change in the insulating properties thereof.

4. The method of claim 1, wherein the step of irradiating a separate second region is conducted simultaneously with the step of irradiating the first region.

5. The method of claim 1, further comprising the step of adjusting at least one of the ion density on the second region and the etching process so that said macroscopic change occurs when the second region reaches a porosity of $P \approx 0.7$, the microholes originating from the individual nuclear traces in the first region having attained the predetermined diameter when the second region has a porosity of $P \approx 0.7$.

6. The method of claim 1, further comprising the step of adjusting at least one of the ion density on the second region and the etching process so that said macroscopic change occurs when the second region reaches a porosity of $P \approx 1.0$, the microholes originating from the individual traces in the first region having attained the predetermined diameter when the second region has a porosity of $P \approx 1.0$.

7. The method of claim 1, wherein the step of monitoring the progress of the etching comprises monitoring the etching progress to observe a macroscopic change provided by the development of ring holes in the second region.

* * * * *